(12) United States Patent
Kim et al.

(10) Patent No.: US 9,645,119 B2
(45) Date of Patent: May 9, 2017

(54) SYSTEM FOR MEASURING PROPAGATION VELOCITY OF SOUND WAVE AND METHOD OF MEASURING PROPAGATION VELOCITY OF SOUND WAVE

(71) Applicant: Korea Institute of Geoscience and Mineral Resources, DaeJeon (KR)

(72) Inventors: Gil Young Kim, DaeJeon (KR); Dae Choul Kim, Busan (KR); Young Kyo Seo, Busan (KR); Gwang Soo Lee, DaeJeon (KR)

(73) Assignee: KOREA INSTITUTE OF GEOSCIENCE & MINERAL RESOURCES, Daejeon (KR)

( * ) Notice: Subject to any disclaimer, the term of this patent is extended or adjusted under 35 U.S.C. 154(b) by 255 days.

(21) Appl. No.: 14/558,161

(22) Filed: Dec. 2, 2014

(65) Prior Publication Data
US 2015/0153311 A1  Jun. 4, 2015

(30) Foreign Application Priority Data

Dec. 2, 2013 (KR) .............................. 2013-0148397

(51) Int. Cl.
*G01N 29/07* (2006.01)
(52) U.S. Cl.
CPC ....... *G01N 29/07* (2013.01); *G01N 2291/011* (2013.01); *G01N 2291/102* (2013.01)
(58) Field of Classification Search
CPC ............. G01N 29/07; G01N 2291/011; G01N 2291/102

USPC .......................................................... 73/597
See application file for complete search history.

(56) References Cited

U.S. PATENT DOCUMENTS

| 3,051,927 | A | * | 8/1962 | Mazzagatti | G01V 1/523 310/334 |
|---|---|---|---|---|---|
| 3,485,087 | A | * | 12/1969 | Brech | G01B 17/02 73/615 |
| 5,167,157 | A | * | 12/1992 | Wertz | G01N 29/223 73/627 |
| 2009/0205427 | A1 | * | 8/2009 | Lootens | G01N 29/032 73/602 |
| 2010/0246326 | A1 | * | 9/2010 | Ichigo | G01N 29/12 367/93 |
| 2013/0167648 | A1 | * | 7/2013 | Tokita | A61B 5/0095 73/655 |

FOREIGN PATENT DOCUMENTS

| KR | 10-0258747 | 3/2000 |
|---|---|---|
| KR | 10-0445371 | 8/2004 |
| KR | 10-0612378 | 8/2006 |
| KR | 10-1248829 | 3/2013 |

* cited by examiner

*Primary Examiner* — J M Saint Surin
(74) *Attorney, Agent, or Firm* — Dentons US LLP

(57) ABSTRACT

The present invention provides an apparatus for measuring the propagation velocity of a sound wave that may easily and accurately measure the propagation velocity of a sound wave in the horizontal and vertical directions of the sample by using the fixing unit preventing the measurement unit from vibrating and the distance measurement unit capable of accurately measuring the distance between the sound wave transmission and reception units, and a method of measuring the propagation velocity of a sound wave by using the apparatus.

11 Claims, 5 Drawing Sheets

SYSTEM FOR MEASURING PROPAGATION VELOCITY OF SOUND WAVE AND METHOD OF MEASURING PROPAGATION VELOCITY OF SOUND WAVE

CROSS-REFERENCE TO RELATED APPLICATION

This application claims priority to Korean Patent Application No. 10-2013-0148397 filed on Dec. 2, 2013 and all the benefits accruing therefrom under 35 U.S.C. §119, the contents of which are incorporated by reference in their entirety to the extent permitted by law.

BACKGROUND OF THE INVENTION

The present disclosure relates to an apparatus for measuring the propagation velocity of a sound wave, and more particularly, to a system for measuring the propagation velocity of a sound wave that may easily and accurately measure the propagation velocity of a sound wave passing through many sample materials such as marine sediment, and a method of measuring the propagation velocity of a sound wave by using the system.

Also, the present invention relates to a system for measuring the propagation velocity of a sound wave that may easily and accurately measure the propagation velocity of a sound wave passing through many materials such as a sample of marine sediment by using a fixing unit for preventing a measurement unit from vibrating and a distance measurement unit capable of accurately measuring the distance between ultrasonic transmission and reception units, and a method of measuring the propagation velocity of a sound wave by using the system.

In addition, the present invention relates to a system for measuring the propagation velocity of a sound wave that may easily and accurately measure the propagation velocity of a sound wave in the horizontal and vertical directions of the sample by using a typical sampling case for collecting a sample of marine sediment as it is, and a method of measuring the propagation velocity of a sound wave by using the system.

In general, collecting and analyzing marine sediment, examining the physical property of the marine sediment, and utilizing such a matter as fundamental data for studying geosciences and mineral resources are very important in studying the geosciences and mineral resources.

However, there are many difficulties in going down to the sea bottom of corresponding seas and analyzing sediment in order to examine the physical property of such marine sediment.

Thus, in order to solve such a difficulty, a method is being mainly used so far in which a sample of marine sediment is collected and carried to the laboratory, and measurement is then performed on the sample of marine sediment to analyze the property of sediment on a corresponding region.

In this example, when a sample is collected from a sedimentary layer located at the sea bottom, carrying a collected sample to the laboratory while maintaining its original state if possible is very important in addition to the collection of the sample.

Also, as an analysis method on the sample of marine sediment collected by using the method as described above, a method of acoustically measuring and analyzing the physical property of marine sediment by using acoustic equipment using a sound wave is being mainly used recently as a result of active research and development of such measurement equipment.

More particularly, in order to measure the thickness of the sedimentary layer located at the sea bottom by using the sound wave, work finding the propagation velocity of the sound wave that is different from one layer to another should be first performed.

That is, the propagation velocity of the sound wave through the marine sediment is needed for the analysis of an association with diagenesis or another physical property but the propagation velocity itself is recognized as important, and in this example, an appropriate velocity structure may be calculated through data analysis on an seismic wave but typical measurement apparatus and methods have had a big difference from real measurements in many cases.

In particular, accurately measuring the propagation velocity of the sound wave on the marine sediment is needed in order to calculate acoustic impedance directly connected to an accurate reflection surface location and a reflection coefficient, and to this end, sampling on a selective core sample should be first performed to be capable of measuring the propagation velocity of the sound wave depending on each depth on a marine sediment core sample obtained from the marine sediment, and then accurate measurement should be performed through the sample obtained in such a way.

In this example, the selective sampling on the core sample as described above may be easily performed by Korean Patent Application No. 10-2012-0100371, filed on Sep. 11, 2012 by the inventors and applicants of the present invention, entitled "SAMPLING CASE FOR MEASURING PROPAGATION VELOCITY OF SOUND WAVE OF MARINE SEDIMENT AND SAMPLING DEVICE INCLUDING THE SAMPLING CASE", for example.

More particularly, Korean Patent Application No. 10-2012-0100371, entitled "SAMPLING CASE FOR MEASURING PROPAGATION VELOCITY OF SOUND WAVE OF MARINE SEDIMENT AND SAMPLING DEVICE INCLUDING THE SAMPLING CASE" as mentioned above relates to a sampling device that includes a sampling case having a hole on each surface to be capable of collecting some samples from core samples obtained by boring a hole though the marine sediment and measuring the propagation velocity of the sound wave in the horizontal and vertical directions from the samples collected, and a plurality of cases capable of being positioned to collect a plurality of samples from a desired location on a core sample and perform depth-dependent sampling.

Thus, by using Korean Patent Application No. 10-2012-0100371, entitled "SAMPLING CASE FOR MEASURING PROPAGATION VELOCITY OF SOUND WAVE OF MARINE SEDIMENT AND SAMPLING DEVICE INCLUDING THE SAMPLING CASE" as mentioned above, a sample is easily collected from the sedimentary layer at the sea bottom and a collected sample is placed on a measurement apparatus so that the sound wave is measured in the vertical and horizontal direction.

Also, an example of a typical measurement apparatus for measuring the sound wave of a sample includes Korean Patent No. 10-0445371 published on Aug. 12, 2004, entitled "SEISMIC WAVE VELOCITY MEASUREMENT SYSTEM FOR UNCONSOLIDATED SEDIMENT CORES".

More particularly, Korean Patent No. 10-0445371, entitled "SEISMIC WAVE VELOCITY MEASUREMENT SYSTEM FOR UNCONSOLIDATED SEDIMENT CORES" as mentioned above relates to an apparatus for measuring the propagation velocity of a seismic wave of an unconsolidated sedimentary layer by using the P wave of seismic waves, and includes a sound generation unit including an instantaneous sound generator, a high-voltage generator and a pre-amplifier, a transmission and reception unit including oscilloscope sensing a signal to represent the signal on cathode ray tube (CRT), a sample holder for holding the shape of the sample and a transceiver including piezoelectrics, and a display unit connected to personal computer (PC).

However, the measuring system of Korean Patent No. 10-0445371 as mentioned above has limitations in that since a measurement unit measuring by holding the sample to transmit and receive an ultrasonic wave is configured to play only a role in simply fixing the sample holder between transmission and reception units, a separate fixing unit for fixing the measurement unit itself is not installed and a separate distance measurement unit for checking an accurate distance between transmission and reception units is not installed either.

That is, when the sound wave is measured, the measurement apparatus should be rigidly fixed so that a measurement is not affected by the vibration of the measurement apparatus, and when a distance between the transmission and reception units varies depending on the size of a sample held between the transmission and reception units, such a change in distance also affects a measurement result. Thus, exactly knowing the distance between the transmission and reception units to reflect the distance to a measurement result is needed but typical measurement apparatuses generally focus on holding the sample to measure an ultrasonic wave and the measurement system allowing the measurement apparatus itself to be fixed and allowing the distance between the transmission and reception units to be measured has not been presented.

Thus, in order to more accurately measure the sound wave on a sample as described above, a measurement system that includes a fixing unit for preventing a sound wave measurement apparatus from vibrating and a distance measurement unit capable of accurately measuring a distance between ultrasonic transmission and reception units should be provided but a measurement system or measurement method that satisfies such a need has not been presented.

In addition, in measuring the propagation velocity of a sound wave, when both the fixing unit for preventing the measurement unit from vibrating and the distance measurement unit capable of accurately measuring the distance between the ultrasonic transmission and reception units as described above are installed and it is possible to install a typical sampling case for collecting a sample of marine sediment on the measurement unit as it is to measure the propagation velocity of a sound wave in the horizontal and vertical directions of the sample, it is contemplated that measurement work is very easy and accurate measurement is possible. However, a measurement system or measurement method that satisfies all of such needs has not been presented.

SUMMARY OF THE INVENTION

The present disclosure provides a system for measuring the propagation velocity of a sound wave that may easily and accurately measure the propagation velocity of a sound wave passing through many materials such as a sample of marine sediment by using a fixing unit for preventing a measurement unit from vibrating and a distance measurement unit capable of accurately measuring the distance between ultrasonic transmission and reception units, and a method of measuring the propagation velocity of a sound wave by using the system.

In addition, the present disclosure also provides a system for measuring the propagation velocity of a sound wave that may easily and accurately measure the propagation velocity of a sound wave by using a typical sampling case for collecting a sample of marine sediment as it is, and a method of measuring the propagation velocity of a sound wave by using the system.

In accordance with an exemplary embodiment of the present invention, a system for measuring a propagation velocity of a sound wave configured to accurately measure a propagation distance of a sound wave passing through a sample material and prevent vibration upon measurement includes: a sound wave configured to generate unit generating a sound wave for measuring a propagation velocity of the sound wave; a measurement unit configured to hold a sample and measure the sample by using the sound wave generated from the sound wave generation unit; and an analysis unit analyzing the sample based on a result measured by the measurement unit.

The sound wave generation unit may include: a sound wave generator configured to generate the sound wave; an amplifier configured to amplify the sound wave generated by the sound wave generator; and an oscilloscope configured to represent a waveform of the sound wave generated by the sound wave generator.

The measurement unit may include: a sound wave transmission unit configured to transmit the sound wave from the sound wave generation unit to the sample; a sound wave reception unit configured to receive the sound wave passing through the sample; a height adjustment unit configured to vertically move the sound wave reception unit by adjusting a distance between the sound wave transmission unit and the sound wave reception unit to hold the sample between the sound wave transmission unit and the sound wave reception unit; an adjustment handle configured to operate the height adjustment unit; a distance measurement unit configured to measure the distance between the sound wave transmission unit and the sound wave reception unit depending on a location of the height adjustment unit; and at least one fixing unit configured to fix the measurement unit to prevent vibration.

The sound wave transmission unit and the sound wave reception unit may be configured in such a manner that an ultrasonic sender sending an ultrasound is installed attachably/detachably by a setscrew in a recess.

The distance measurement unit may include a ruler including gradations to measure the distance between the sound wave transmission unit ad the sound wave reception unit.

The distance measurement unit may include a separate display device on which a location of the distance measurement unit is displayed.

The distance measurement unit may include: a ruler gradations to measure the distance between the sound wave transmission unit ad the sound wave reception unit; and a separate display device on which a location of the distance measurement unit is displayed.

The measurement unit may be configured to collect the sample by using a sampling case pre-manufactured to collect a sample of sediment and then install the sampling case between the sound wave transmission unit and the sound wave reception unit to perform measurement.

The system may be configured to: fix the measurement unit by the fixing unit of the measurement unit, place the sample on the sound wave transmission unit, and then rotate the adjustment handle to move the height adjustment unit down to hold the sample between the sound wave transmission unit and the sound wave reception unit until the sound wave reception unit is in contact with the sample, measure the distance between the sound wave transmission unit and the sound wave reception unit through the distance measurement unit after the sample is installed, transmit a sound wave by the sound wave transmission unit and receive the sound wave by the sound wave reception unit after the passing of the sample, when the sound wave generated from the sound wave generation unit is propagated to the sound wave transmission unit through a cable, analyze the sample by the analysis unit based on a propagation time for which the sound wave passes through the sample from the sound wave transmission unit and is received by the sound wave reception unit.

The analysis unit may include a computer on which a program configured to perform a series of processing operations is executed, or dedicated hardware configured to the processing operations, wherein the processing operations may include receiving information on unique properties including an amplitude and propagation time of the sound wave generated from the sound wave generation unit and a propagation time measured from the measurement unit to calculate a sound wave propagation velocity by a time difference, and analyzing the properties of the sample based on the sound wave propagation velocity.

In accordance with another exemplary embodiment of the present invention, a method of measuring a propagation velocity of a sound wave by using the system includes: fixing the measurement unit of the system by using a fixing unit; placing a sample on the sound wave transmission unit of the measurement unit; holding the sample between the sound wave transmission unit and the sound wave reception unit by rotating the adjustment handle of the height adjustment unit of the measurement unit to move the sound wave reception unit down, until the sound wave reception unit of the measurement unit is in contact with the sample; measuring a distance between the sound wave transmission unit and the sound wave reception unit through the distance measurement unit of the measurement unit; propagating the sound wave generated from the sound wave generation unit of the system through a cable to the sound wave transmission unit, and measuring a propagation time for which the sound wave passes through the sample from the sound wave transmission unit and is received by the sound wave reception unit; and analyzing the sample by the analysis unit of the system based on the propagation time measured.

The placing of the sample and the holding of the sample may be configured to collect the sample by using a sampling case pre-manufactured to collect a sample of sediment and then install the sampling case between the sound wave transmission unit and the sound wave reception unit to perform measurement.

BRIEF DESCRIPTION OF THE DRAWINGS

Exemplary embodiments can be understood in more detail from the following description taken in conjunction with the accompanying drawings, in which.

DETAILED DESCRIPTION OF THE PRESENTLY PREFERRED EMBODIMENTS

Particular embodiments of a system for measuring the propagation velocity of a sound wave (hereinafter, referred to as a "sound wave propagation velocity measurement system") and a method of measuring the propagation velocity of a sound wave (hereinafter, referred to as a "sound wave propagation velocity measurement method") by using the system according to the present invention are described below with reference to the attached drawings.

It should be noted that descriptions disclosed herein are only an embodiment for practicing the present invention, and the present invention is not limited to the following embodiments.

Also, in describing the embodiments of the present invention, it should be noted that content determined to be the same or similar as the related art or easily understood and practiced by a person skilled in the art has not been provided for the simplicity of description.

That is, the present invention relates to a sound wave propagation velocity measurement system that may easily and accurately measure the propagation velocity of a sound wave passing through a sample material by using a fixing unit for preventing a measuring unit from vibrating and a distance measuring unit capable of accurately measuring the distance between ultrasonic transmission and reception units, and a sound wave propagation velocity measurement method using the system, as will be described below.

In addition, the present invention relates to a sound wave propagation velocity measurement system that may easily and accurately measure the propagation velocity of a sound wave by using a typical sampling case for collecting a sample of marine sediment as it is, and a sound wave propagation velocity measurement method using the system, as will be described below.

Subsequently, particular embodiments of a sound wave propagation velocity measurement system and a sound wave propagation velocity measurement method using the system according to the present invention are described with reference to the attached drawings.

Figure 1:
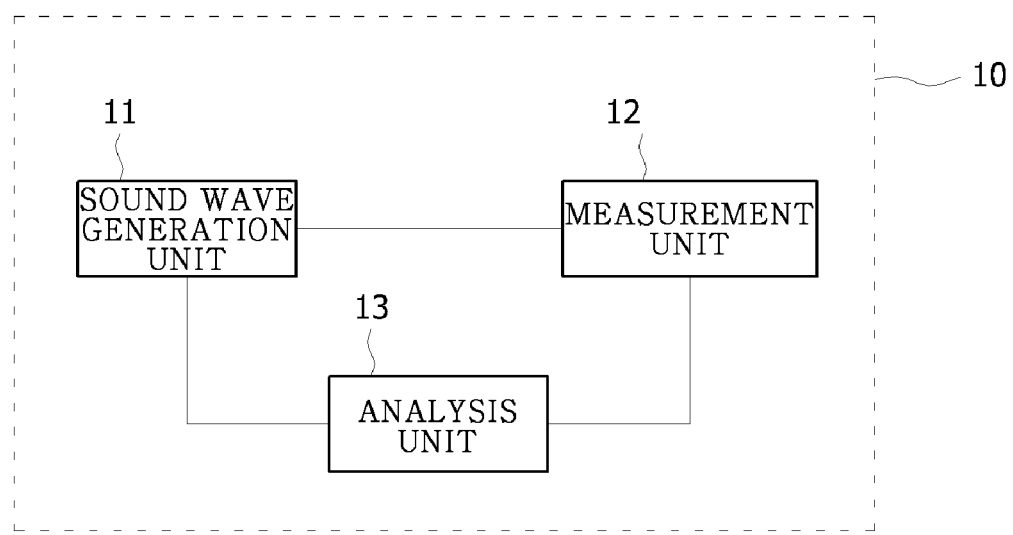
FIG. 1 is a block diagram schematically representing a whole configuration of a system for measuring the propagation velocity of a sound wave (hereinafter, referred to as a "sound wave propagation velocity measurement system") according to an embodiment of the present invention.

First, FIG. 1 is a block diagram schematically representing a whole configuration of a sound wave propagation velocity measurement system 10 according to an embodiment of the present invention.

As shown in FIG. 1, the sound wave propagation velocity measurement system 10 generally includes a sound wave generation unit 11 generating a sound wave for measurement, a measurement unit 12 holding a sample and measuring the sample by using the sound wave generated from the sound wave generation unit 11, and an analysis unit 13 analyzing the sample based on a result measured by the measurement unit.

Figure 2:
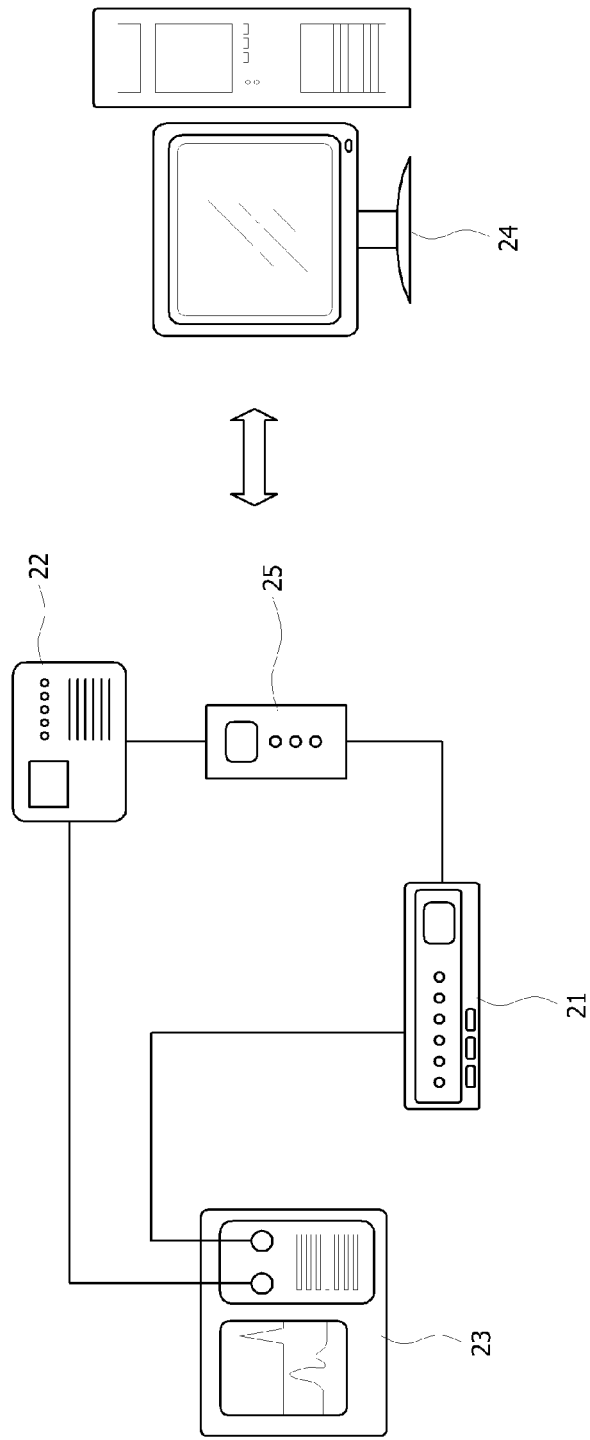
FIG. 2 is a diagram simply representing whole configurations of a sound wave generation unit and an analysis unit of the sound wave propagation velocity measurement system according to the embodiment of the present invention as represented in FIG. 1.

Also, FIG. 2 is a diagram simply representing whole configurations of the sound wave generation unit 11 and the analysis unit 13 of the sound wave propagation velocity measurement system 10 according to the embodiment of the present invention as represented in FIG. 1.

That is, as shown in FIG. 2, the sound wave generation unit 11 may include, for example, a sound wave generator 21 for generating a sound wave, an amplifier amplifying the sound wave generated by the sound wave generator 21, and oscilloscope 23 representing the waveform of the sound wave generated by the sound wave generator.

In addition, the analysis unit 13 may include a computer 24 on which a program configured to perform a series of processing operations is executed, or dedicated hardware configured to such processing operations. The processing operations include receiving information on unique properties such as an amplitude and propagation time of the sound wave generated from the sound wave generation unit 11 and a propagation time measured from the measurement unit 12 to calculate a sound wave propagation velocity by a time difference, and analyzing the properties of the sample based on the sound wave propagation velocity obtained by using such a method.

More particularly, the sound wave propagation velocity measurement system 10 may be configured to directly input the sound wave generated from the sound wave generator 21 to the channel 1 of the oscilloscope 23, have the sound wave generation unit 11 so that the sound wave passing through the sample 25 through the measurement unit 12 is input to the channel 2 of the oscilloscope 23, connect the oscilloscope 23 of the sound wave generation unit 11 as described above to the computer 24 of the analysis unit 13 to automatically display a waveform, amplitude and propagation time of each sound wave through a display device such as a monitor installed at the analysis unit 13, and calculate a sound wave propagation velocity to analyze the property of the sample, as shown in FIG. 2.

In this example, configurations of the sound wave generation unit 11 and the analysis unit 13 described above with reference to FIG. 2 are only embodiments for describing the present invention, and the present invention may appropriately change the configurations of the sound wave generation unit 11 and the analysis unit 13 as needed. For example, the sound wave generation unit and the analysis unit may be configured to change a generated sound wave or change a processing algorithm for analyzing the sample.

In addition, the measurement unit 12 is configured to be capable of easily and accurately measuring the propagation velocity of the sound wave passing through the sample material by using a fixing unit for preventing vibration and a distance measuring unit capable of accurately measuring the distance between ultrasonic transmission and reception units, as will be described FIGS. 3 and 4.

Subsequently, a particular configuration of the measurement unit 12 of the sound wave propagation velocity measurement system according to an embodiment of the present invention is described in detail with reference to FIGS. 3 and 4.

Figure 3:
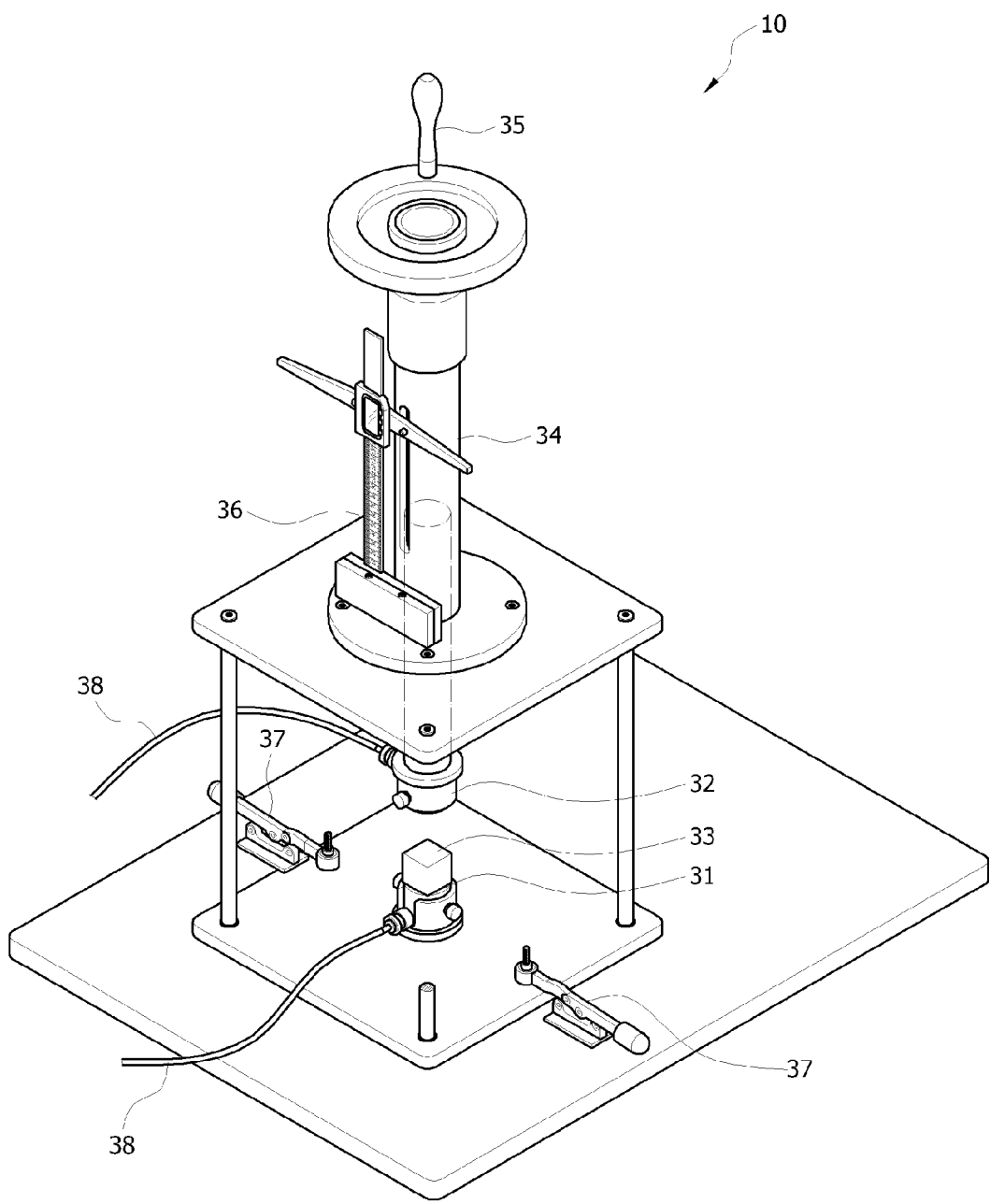
FIG. 3 is a perspective view of a whole configuration of a measurement unit of the sound wave propagation velocity measurement system according to the embodiment of the present invention as represented in FIG. 1.
Figure 4:
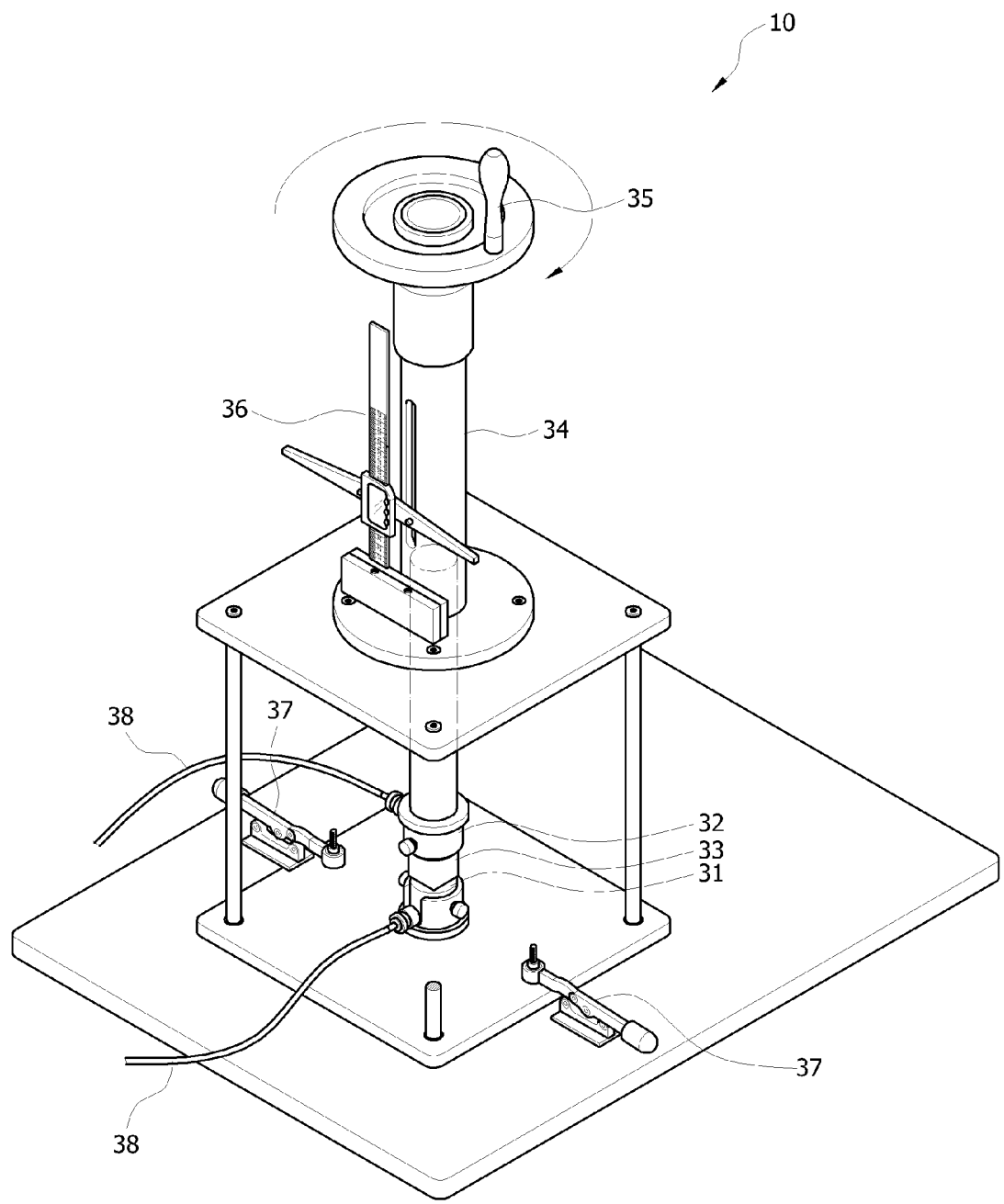
FIG. 4 is a perspective view of a whole configuration of a measurement unit of the sound wave propagation velocity measurement system according to the embodiment of the present invention as represented in FIG. 1.

That is, FIG. 3 is a perspective view of a whole configuration of the measurement unit 12 of the sound wave propagation velocity measurement system according to the embodiment of the present invention as represented in FIG. 1, and FIG. 4 is a perspective view of a whole configuration of the measurement unit 12 of the sound wave propagation velocity measurement system according to the embodiment of the present invention as represented in FIG. 1.

More particularly, as shown in FIGS. 3 and 4, the measurement unit 12 of the sound wave propagation velocity measurement system 10 includes a sound wave transmission unit 31, a sound wave reception unit 32, a sample 33 held between the sound wave transmission unit 31 and the sound wave reception unit 32, a height adjustment unit 34 configured to be capable of vertically moving the sound wave reception unit 32 to adjust the distance between the sound wave transmission unit 31 and the sound wave reception unit 32 and hold the sample 33 inbetween, an adjustment handle 35 for operating the height adjustment unit 34, a distance measurement unit 36 for measuring the distance between the sound wave transmission unit 31 and the sound wave reception unit 32 depending on the location of the height adjustment unit 34, and at least one fixing unit 37 fixing the measurement unit 32 to a table in order to prevent vibration.

In this example, the sample 33 held between the sound wave transmission unit 31 and the sound wave reception unit 32 may be measured by using a sampling case disclosed in Korean Patent Application No. 10-2012-0100371, entitled "SAMPLING CASE FOR MEASURING PROPAGATION VELOCITY OF SOUND WAVE OF MARINE SEDIMENT AND SAMPLING DEVICE INCLUDING THE SAMPLING CASE" as it is.

Also, the sound wave transmission unit 31 and the sound wave reception unit 32 may be configured such that an ultrasonic sender and receiver sending and receiving an ultrasound may be attachably/detachably installed by a setscrew in a recess, as represented in FIGS. 3 and 4.

In this case, a cable 38 enabling a connection to an external device is connected to the ultrasonic sender and receiver, as represented in FIGS. 3 and 4.

In addition, the distance measurement unit 36 may be configured simply in the form of a ruler including gradations to enable the distance between the sound wave transmission unit 31 and the sound wave reception unit 32 to be measured, may be configured such that a corresponding location is automatically displayed by using a separate display device, or may be configured to include the two configurations above as needed.

Subsequently, a particular operation of the sound wave propagation velocity measurement system 10 according to the embodiment of the present invention as described above is described.

First, the measurement unit 32 is fixed by the fixing unit 37 and then the sample 33 or the sampling case is placed on the sound wave transmission unit 31.

Subsequently, until the sound wave reception unit 32 is in contact with the sample or the sampling case, the adjustment handle 35 is rotated to move the height adjustment unit 34 down so that the sample 33 or the sampling case is placed between the sound wave transmission unit 31 and the sound wave reception unit 32.

In this case, after the sample 33 or the sampling case has been placed, the location of the height adjustment unit 34 is measured through the distance measurement unit 36 so that it is possible to accurately measure the distance between the sound wave transmission unit 31 and the sound wave reception unit 32.

Next, the sound wave generated from the sound wave generation unit 11 is propagated to the sound wave transmission unit 31 through the cable 38 so that a propagation time of the sound wave corresponding to a time for which the sound wave passes through the sample 33 from the sound wave transmission unit 31 and is received by the sound wave reception unit 32, and by performing analysis by the analysis unit 13 based on the propagation time of the sound wave measured, it is possible to perform accurate analysis on the sample 33.

Figure 5:
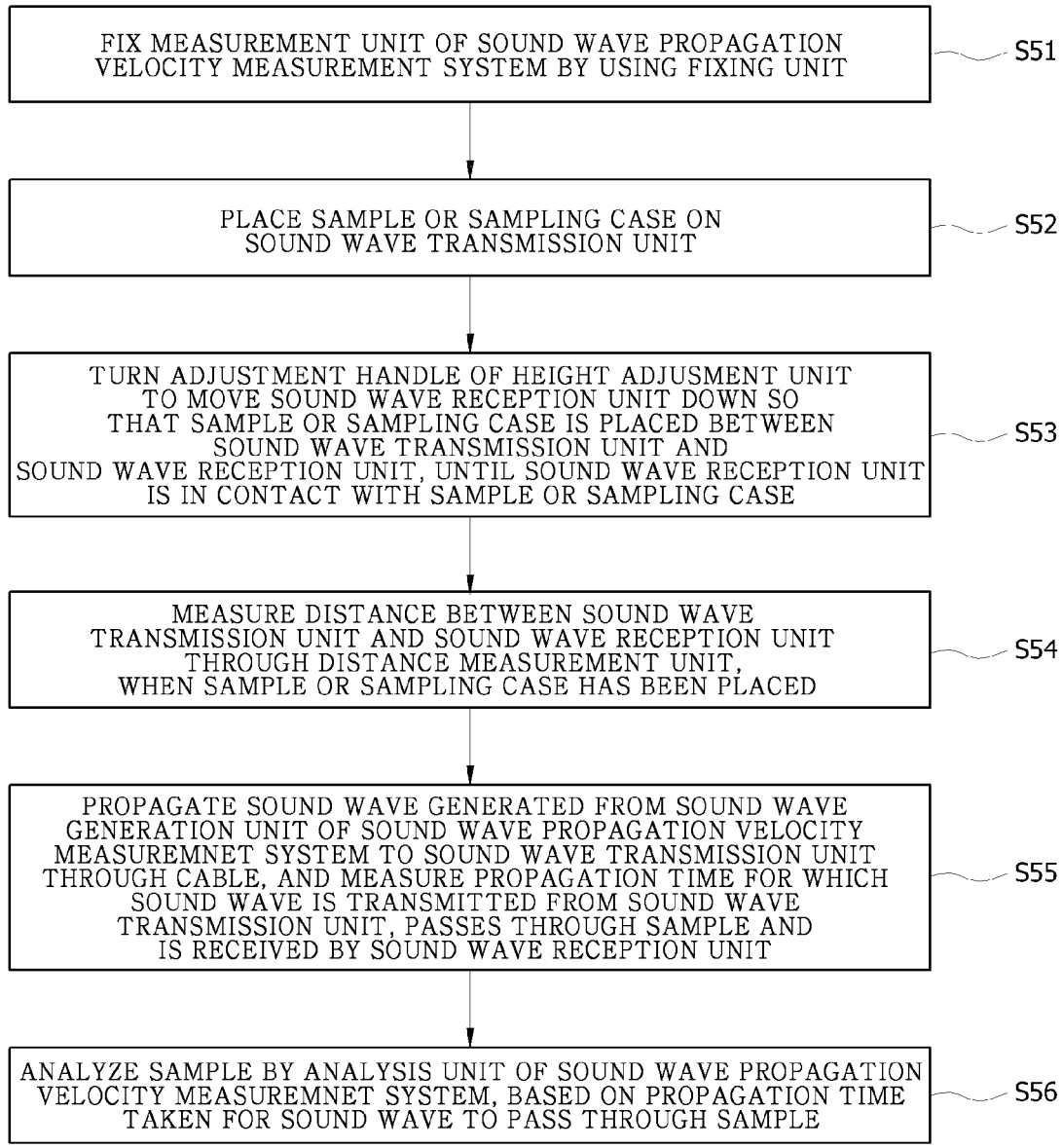
FIG. 5 is a flowchart simply representing a whole configuration of a method of measuring the propagation velocity of a sound wave by using the sound wave propagation velocity measurement system according to the embodiment of the present invention as represented in FIG. 1.

Also, FIG. 5 is a flowchart simply representing a whole configuration of a sound wave propagation velocity measurement method performed by using the sound wave propagation velocity measurement system 10 according to the embodiment of the present invention as described above.

That is, according to the sound wave propagation velocity measurement method using the sound wave propagation velocity measurement system 10 according to the embodiment of the present invention as described above, a fixing unit is first used to fix a measurement unit in step S51, and then a sample or a sampling case is placed on a sound wave transmission unit in step S52.

Next, until a sound wave reception unit is in contact with a sample, an adjustment handle of a height adjustment is rotated to move the sound wave reception unit down so that the sample or the sampling case is placed between the sound wave transmission unit and the sound wave reception unit in step S53, and when the sample or the sampling case has been placed, the distance between the sound wave transmission unit and the sound wave reception unit is measured through a distance measurement unit in step S54.

Subsequently, a sound wave generated from a sound wave generation unit is propagated to the sound wave transmission unit through a cable, a propagation time for which the sound wave is transmitted from the sound wave transmission unit, passes through the sample and is received by the sound wave reception unit is measured in step S55 and then, analysis on the sample is performed by an analysis unit based on the propagation time taken for the sound wave to pass through the sample in step S56.

In this example, particular content of the sound wave generation unit generating the sound wave and a method of analyzing the sample by the analysis unit based on the sound wave propagation time is obvious to a person skilled in the art when the above descriptions and related art are referenced. Thus, detailed descriptions thereof are not provided in this embodiment.

Thus, it is possible to implement a sound wave propagation velocity measurement system and a sound wave propagation velocity measurement using the system according to the present invention, and by implementing the sound wave propagation velocity measurement system and the sound wave propagation velocity measurement using the system according to the present invention, the present invention may prevent a measurement unit from vibrating, and accurately measure the distance between the sound wave transmission unit and the sound wave reception unit and thus easily and accurately measure the propagation velocity of the sound wave passing through many materials such as a sample of marine sediment.

Also, according to the present invention, since it is possible to use a typical sampling case for collecting the sample of marine sediment as it is, it is possible to easily and accurately measure the sound wave propagation velocity in the horizontal and vertical directions of the sample.

Although the sound wave propagation velocity measurement system and the sound wave propagation velocity measurement method using the system according to the present invention have been described in detail through embodiments of the present invention as described above, the present invention is not limited to content in the embodiments and may have many modifications, changes, combinations and replacements depending on design and other factors by a person skilled in the art.

What is claimed is:

1. A system for measuring a propagation velocity of a sound wave configured to accurately measure a propagation distance of a sound wave passing through a sample material and prevent vibration upon measurement, the system comprising:
  a sound wave generator to generate a sound wave for measuring a propagation velocity of the sound wave;
  a measurement unit to hold a sample and measure the sample by using the sound wave generated from the sound wave generation unit; and
  an analysis unit to analyze the sample based on a result measured by the measurement unit,
  wherein the measurement unit comprises:
    a sound wave transmission unit to transmit the sound wave from the sound wave generation unit to the sample,
    a sound wave reception unit to receive the sound wave passing through the sample,
    a height adjustment unit to vertically move the sound wave reception unit by adjusting a distance between the sound wave transmission unit and the sound wave reception unit to hold the sample between the sound wave transmission unit and the sound wave reception unit,
    an adjustment handle to operate the height adjustment unit,
    a distance measurement unit to measure the distance between the sound wave transmission unit and the sound wave reception unit depending on a location of the height adjustment unit; and
    at least one fixing unit to fix the measurement unit to prevent vibration.

2. The system of claim 1, wherein the sound wave generation unit comprises:
  an amplifier to amplify the sound wave generated by the sound wave generator; and
  an oscilloscope to represent a waveform of the sound wave generated by the sound wave generator.

3. The system of claim 1, wherein the sound wave transmission unit and the sound wave reception unit are configured in such a manner that an ultrasonic sender is attachably/detachably secured by a setscrew in a recess.

4. The system of claim 1, wherein the distance measurement unit comprises a ruler with gradations to measure the distance between the sound wave transmission unit and the sound wave reception unit.

5. The system of claim 1, wherein the distance measurement unit comprises a separate display device on which a location of the distance measurement unit can be displayed.

6. The system of claim 1, wherein the distance measurement unit comprises:
  ruler gradations to measure the distance between the sound wave transmission unit and the sound wave reception unit; and
  a separate display device on which a location of the distance measurement unit can be displayed.

7. The system of claim 1, wherein the measurement unit is configured to collect the sample by using a sampling case that is pre-manufactured to collect a sample of sediment and then accept the sampling case between the sound wave transmission unit and the sound wave reception unit.

8. The system of claim 1, wherein the system is configured to:

fix the measurement unit by the fixing unit of the measurement unit, place the sample on the sound wave transmission unit, and then rotate the adjustment handle to move the height adjustment unit down to hold the sample between the sound wave transmission unit and the sound wave reception unit until the sound wave reception unit is in contact with the sample, after the sample is installed, measure the distance between the sound wave transmission unit and the sound wave reception unit through the distance measurement unit, transmit a sound wave by the sound wave transmission unit and receive the sound wave by the sound wave reception unit after the passing through the sample, the sound wave generated from the sound wave generation unit being propagated to the sound wave transmission unit via a cable, and analyze the sample using the analysis unit based on a propagation time for the sound wave to pass through the sample.

9. The system of claim 1, wherein:

the analysis unit comprises (a) a computer with programmed instructions configured to perform a series of processing operations is executed, or (b) dedicated hardware with logic configured to perform the processing operations, the processing operations comprise receiving information on unique properties to calculate a sound wave propagation velocity by a time difference, and analyzing the properties of the sample based on the sound wave propagation velocity, and the unique properties comprise an amplitude and propagation time of the sound wave generated from the sound wave generation unit and a propagation time measured from the measurement unit.

10. A method of measuring a propagation velocity of a sound wave by using the system according to any of claims 1, 2, and 3 to 9 the method comprising the steps of:

fixing the measurement unit of the system by using a fixing unit;

placing a sample on the sound wave transmission unit of the measurement unit;

holding the sample between the sound wave transmission unit and the sound wave reception unit by rotating the adjustment handle of the height adjustment unit of the measurement unit to move the sound wave reception unit down, until the sound wave reception unit of the measurement unit is in contact with the sample;

measuring a distance between the sound wave transmission unit and the sound wave reception unit through the distance measurement unit of the measurement unit;

propagating the sound wave generated from the sound wave generation unit of the system through a cable to the sound wave transmission unit, and measuring a propagation time for which the sound wave passes through the sample from the sound wave transmission unit and is received by the sound wave reception unit; and analyzing the sample by the analysis unit of the system based on the propagation time measured.

11. The method of claim 10, wherein the placing of the sample and the holding of the sample including collecting the sample by (a) using a sampling case pre-manufactured to collect a sample of sediment and then (b) installing the sampling case between the sound wave transmission unit and the sound wave reception unit.

* * * * *